(12) United States Patent
Vidal et al.

(10) Patent No.: US 7,044,987 B2
(45) Date of Patent: May 16, 2006

(54) 6-ALKOXY-2,3-DIAMINOPYRIDINE COUPLERS IN WHICH THE AMINO RADICAL IN POSITION 2 IS A MONOSUBSTITUTED AMINO RADICAL, AND USE OF THESE COUPLERS FOR DYEING KERATIN FIBRES

(75) Inventors: Laurent Vidal, Paris (FR); Aziz Fadli, Chelles (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/678,634

(22) Filed: Oct. 6, 2003

(65) Prior Publication Data

US 2005/0060814 A1 Mar. 24, 2005

Related U.S. Application Data

(60) Provisional application No. 60/431,753, filed on Dec. 9, 2002.

(30) Foreign Application Priority Data

Oct. 4, 2002 (FR) .................................. 02 12354

(51) Int. Cl.
*A61K 7/13* (2006.01)
(52) U.S. Cl. .................. 8/405; 8/406; 8/408; 8/409; 8/410; 8/411; 8/421; 8/568; 8/602; 546/249; 546/250
(58) Field of Classification Search ............. 8/405, 8/406, 408, 409, 410, 411, 421, 568, 602; 546/249, 250
See application file for complete search history.

(56) References Cited

U.S. PATENT DOCUMENTS

| | | | |
|---|---|---|---|
| RE30,199 E | 1/1980 | Rose et al. ............... 8/10.2 |
| 4,784,667 A * | 11/1988 | Maak et al. ............... 8/409 |
| 4,823,985 A | 4/1989 | Grollier et al. ............. 222/1 |
| 5,061,289 A | 10/1991 | Clausen et al. ............. 8/405 |
| 5,380,340 A | 1/1995 | Neunhoeffer et al. ...... 8/409 |
| 5,766,576 A | 6/1998 | Löwe et al. ............... 424/62 |
| 5,769,903 A * | 6/1998 | Audousset et al. ......... 8/409 |
| 5,785,717 A * | 7/1998 | Maubru et al. ............. 8/409 |
| 6,099,592 A | 8/2000 | Vidal et al. ............... 8/409 |
| 6,692,540 B1 * | 2/2004 | Audousset ................. 8/409 |
| 6,730,789 B1 | 5/2004 | Birault et al. ............. 546/121 |
| 6,837,908 B1 * | 1/2005 | Vidal et al. ............... 8/405 |

FOREIGN PATENT DOCUMENTS

| | | |
|---|---|---|
| DE | 23 59 399 | 6/1975 |
| DE | 32 33 540 A1 | 3/1984 |
| DE | 38 43 892 A1 | 6/1990 |
| DE | 41 15 148 A1 | 11/1992 |
| DE | 41 33 957 A1 | 4/1993 |
| DE | 195 43 988 A1 | 5/1997 |
| DE | 199 36 442 A1 | 2/2001 |
| EP | 0 728 464 A1 | 8/1996 |
| EP | 0 770 375 A1 | 5/1997 |
| FR | 1 397 551 | 4/1964 |
| FR | 2 586 913 | 3/1987 |
| FR | 2 733 749 | 11/1996 |
| FR | 2 779 952 | 12/1999 |
| FR | 2 801 308 | 5/2001 |
| GB | 1 026 978 | 4/1966 |
| GB | 1 153 196 | 5/1969 |
| JP | 88-169571 | 7/1988 |
| JP | 02019576 A | 1/1990 |
| WO | WO 94/08969 | 4/1994 |
| WO | WO 94/08970 | 4/1994 |
| WO | WO 96/15765 | 5/1996 |
| WO | WO 01/08645 A1 | 2/2001 |

OTHER PUBLICATIONS

Copy of English Abstract for DE 41 15 148 A1.
Copy of English Abstract for EP 0 77 375 A.
Copy of English Abstract for JP 02019576 A.

* cited by examiner

*Primary Examiner*—Eisa Elhilo
(74) *Attorney, Agent, or Firm*—Finnegan, Henderson, Farabow, Garrett & Dunner L.L.P.

(57) ABSTRACT

The invention relates to a dye composition that is useful for dyeing keratin fibres, containing at least one oxidation base and at least one coupler of the 6-alkoxy-2,3-diaminopyridine type in which the amino radical in position 2 is a monosubstituted amino radical, to the use of this composition for dyeing keratin fibres and to the dyeing process using this composition. The invention also relates to novel 6-alkoxy-2,3-diaminopyridine compounds that are useful as couplers.

21 Claims, No Drawings

6-ALKOXY-2,3-DIAMINOPYRIDINE COUPLERS IN WHICH THE AMINO RADICAL IN POSITION 2 IS A MONOSUBSTITUTED AMINO RADICAL, AND USE OF THESE COUPLERS FOR DYEING KERATIN FIBRES

The invention relates to a dye composition hat is useful for dyeing keratin fibres, containing at least one oxidation base and at least one coupler of the 6-alkoxy-2,3-diaminopyridine type in which the amino radical in position 2 is a monosubstituted amino radical, to the use of this composition for dyeing keratin fibres and to the dyeing process using this composition. The invention also relates to novel 6-alkoxy-2,3-diaminopyridine compounds that are useful as couplers.

It is known practice to dye keratin fibres, and in particular human hair, with dye compositions containing oxidation dye precursors, which are generally known as oxidation bases, such as ortho- or para-phenylenediamines, ortho- or para-aminophenols and heterocyclic couplers. These oxidation bases are colourless or weakly coloured compounds which, when combined with oxidizing products, can give rise to coloured compounds by a process of oxidative condensation.

It is also known that the shades obtained with these oxidation bases can be varied by combining them with couplers or coloration modifiers, these agents being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" coloration obtained by means of these oxidation dyes must moreover satisfy a certain number of requirements. Thus, it must have no toxicological drawback, it must allow shades to be obtained in the desired strength, and it must show good fastness with respect to external agents such as light, bad weather, washing, permanent-waving, perspiration and rubbing.

The dyes must also allow white hair to be covered and, finally, they must be as unselective as possible, ie they must produce the smallest possible differences in coloration along the same keratin fibre, which is generally differently sensitized (ie damaged) between its end and its root.

Document FR 1 397 551 describes dye compositions containing oxidation dye precursors of the trisubstituted pyridine derivative type, each of the substituents possibly being a hydroxyl, alkoxy, amino or $NR_1R_2$ radical with $R_1$ and $R_2$ representing a H, alkyl or aryl. The coloration is obtained either by oxidation in air or with an oxidizing medium containing aqueous hydrogen peroxide solution at basic pH. On account of the high oxidizability of these pyridine precursors, the dyeing results obtained on the hair have a tendency to change over time by changing colour, which turns out to be particularly unattractive.

Document DE 3 233 540 proposes hair dye compositions containing, as coupler, 6-alkoxy-3-aminopyridine derivatives substituted in position 2 with an $NH_2$ or $NHR_3$ radical with $R_3$=H, $C_1$–$C_4$ alkyl or $C_2$–$C_4$ hydroxyalkyl in combination with standard oxidation bases. These compositions give, in the presence of certain bases such as para-phenylenediamine or para-toluenediamine, dark blue shades that are unstable to light and that lack strength and uniformity between the root and the end of the hairs.

Documents DE 4 115 148, FR 2 779 952, EP 728 464 and DE 199 36 442 propose to combine particular pyridine-based couplers of this type with specific oxidation bases such as pyrazolopyrimidine, para-aminophenol, pyrimidine or 4,5- or 3,4-diaminopyrazole bases.

However, none of these compositions make it possible to obtain strong colorations in varied shades that are uniform between the root and the end of the hairs, that show little selectivity and particularly good resistance, and that have good chromaticity.

This aim is achieved with the present invention, one subject of which is a dye composition comprising, in a medium that is suitable for dyeing,
at least one oxidation base, and
at least one 6-alkoxy-2,3-diaminopyridine coupler of formula (I) or a corresponding addition salt thereof:

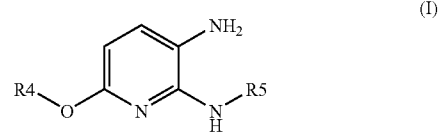

in which:
$R_4$ represents a linear or branched $C_1$–$C_4$ alkyl radical optionally substituted with one or more hydroxyl, $C_1$–$C_2$ alkoxy or $NR_7R_8$ radicals in which $R_7$ and $R_8$ are chosen from hydrogen, a $C_1$–$C_4$ alkyl, a $C_2$–$C_6$ (poly)hydroxyalkyl, a $C_2$–$C_6$ (poly)aminoalkyl or a $C_2$–$C_6$ aminohydroxyalkyl;

$R_5$ represents a linear or branched $C_1$–$C_6$ alkyl radical substituted with one or more radicals chosen from $C_1$–$C_2$ alkoxy, hydroxyl, carboxyl, sulphonic (—$SO_3H$), $NR_9R_{10}$, hydroxyalkoxy, acylamino or halogeno radicals; a 2-hydroxyethyloxyethyl radical; when $R_5$ is an alkyl radical substituted with a hydroxyl or with an alkoxy, $R_5$ carries a second radical;

$R_9$ and $R_{10}$ denote, independently of one another, a hydrogen atom; a $C_1$–$C_4$ alkyl radical which can optionally be substituted with one or more hydroxyl, amino, $C_1$–$C_2$ mono- or dialkylamino, alkoxy or acylamino (RCONH with R representing a $C_1$–$C_4$ alkyl radical) radicals; $R_9$ and $R_{10}$, together with the nitrogen atom to which they are attached, form a heterocycle which can contain one or more nitrogen, oxygen or sulphur atoms.

In the context of the present invention, the term "alkyl" means linear or branched radicals, for example methyl, ethyl, n-propyl, isopropyl, butyl, etc., cycloalkyl radicals, for example cyclobutyl, cyclopentyl, cyclohexyl, etc. An alkoxy radical is a radical alk-O, the alkyl radical having the definition given above.

By way of example, $R_5$ represents an aminoethyl, carboxyethyl, acylaminoethyl, dihydroxyethyl, dihydroxypropyl, 3-aminopropyl, N,N-dimethylaminoethyl, N-methylaminoethyl, 2-hydroxyethylaminoethyl, 2-hydroxyethyloxyethyl, acetamido, (2-hydroxy-1-methyl)ethyl or 2-hydroxypropyl radical.

Preferably, $R_5$ represents a $C_1$–$C_4$ alkyl radical substituted with one or more radicals chosen from hydroxyl, $C_1$–$C_2$ alkoxy, amino, $C_1$–$C_2$ mono- or dialkylamino, carboxyl or sulphonic radicals. Preferably, $R_5$ is chosen from an alkyl radical substituted with an amino or mono- or dialkylamino. According to one particular embodiment, $R_5$ is a disubstituted alkyl radical. In particular, $R_5$ represents a dihydroxyalkyl radical, an acetamidoalkyl radical, a dialkylaminoalkyl radical, an alkyl radical substituted with a hydroxyl and an amino, for example one of the radicals 2-dimethylaminoethyl, 3-dimethylaminopropyl and acetamidoethyl.

In formula (I), $R_4$ preferably represents a $C_1$–$C_4$ alkyl radical optionally substituted with one or more hydroxyl or $C_1$–$C_2$ alkoxy radicals. Preferably, $R_4$ represents a $C_1$–$C_4$ alkyl radical.

The compounds of formula (I) that are useful in the present invention are for example the following compounds:

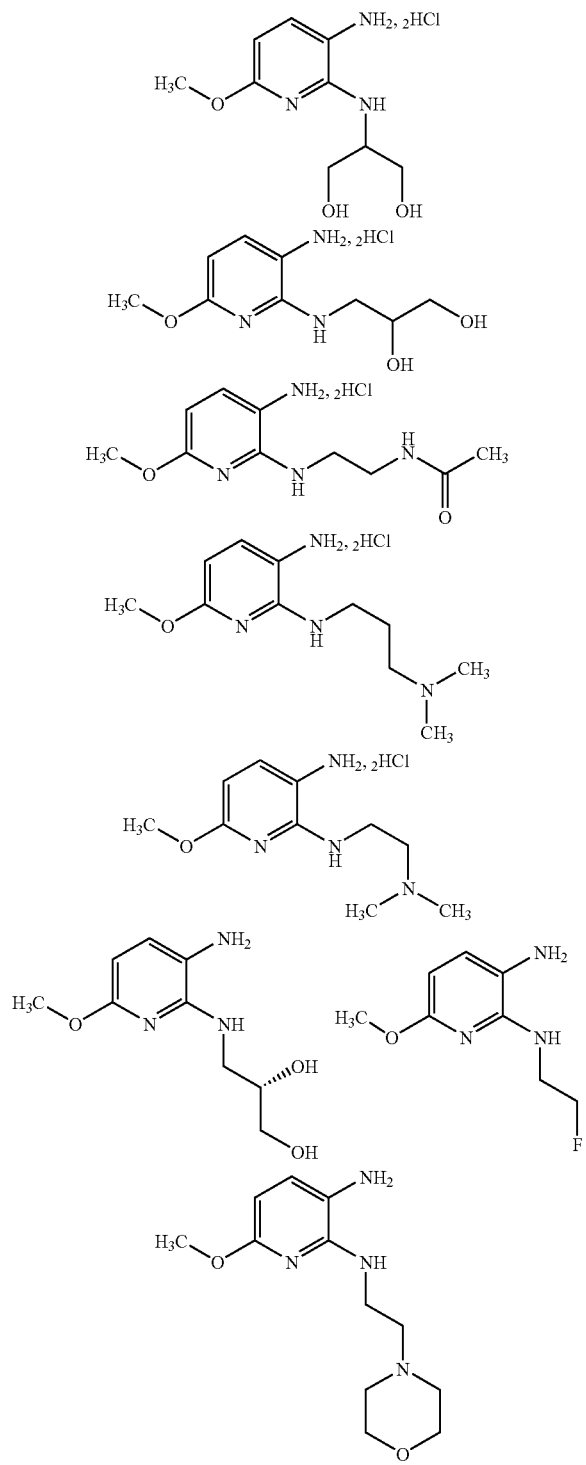

-continued

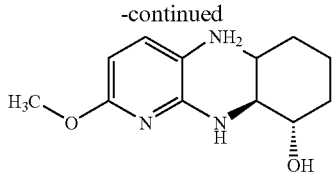

The oxidation dye composition of the present invention comprises one or more oxidation bases conventionally used in oxidation dyeing. By way of example, these oxidation bases are chosen from para-phenylenediamines, bis(phenyl) alkylenediamines, para-aminophenols, bis-para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamino, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazol[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof with an acid or with a base.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

The oxidation base(s) present in the composition of the invention is (are) each generally present in an amount of between 0.001% and 10% by weight approximately, and preferably between 0.005% and 6%, relative to the total weight of the dye composition.

The composition according to the invention may contain one or more additional couplers conventionally used in oxidation dyeing. Among these additional couplers that may especially be mentioned are meta-phenylenediamines, meta-aminophenols, meta-diphenols, naphthalene-based couplers and heterocyclic couplers other than the couplers of formula (I) as defined above, and the addition salts thereof.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the addition salts thereof with an acid.

In the composition of the present invention, the coupler(s) is (are) each generally present in an amount of between 0.001% and 10% by weight approximately, and preferably between 0.005% and 6%, relative to the total weight of the dye composition.

In general, the addition salts of the oxidation bases and of the couplers that may be used in the context of the invention are chosen especially from the addition salts with an acid, such as the hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, aqueous ammonia, amines or alkanolamines.

The dye composition in accordance with the invention may also contain one or more direct dyes that may be chosen especially from nitrobenzene dyes, azo direct dyes and methine direct dyes. These direct dyes may be of nonionic, anionic or cationic nature.

The dye composition of the present invention is particularly useful for dyeing keratin fibres, in particular human keratin fibres. In this case, the medium is a cosmetic medium that is suitable for dyeing these fibres.

This medium that is suitable for dyeing, also known as a dye support, generally consists of water or of a mixture of water and of at least one organic solvent to dissolve the compounds that would not be sufficiently soluble in the water. Examples of organic solvents that may be mentioned include $C_1$–$C_4$ lower alkanols, such as ethanol and isopropanol; polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The solvents are preferably present in proportions preferably of between 1% and 40% by weight approximately and even more preferably between 5% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrating agents, sequestering agents, fragrances, buffers, dispersants, conditioners, for instance volatile or non-volatile, modified or unmodified silicones, film-forming agents, ceramides, preserving agents and opacifiers.

The above adjuvants are generally present in an amount for each of between 0.01% and 20% by weight relative to the weight of the composition.

Needless to say, a person skilled in the art will take care to select this or these additional optional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used for dyeing keratin fibres, or alternatively using standard buffer systems.

Among the acidifying agents that may be mentioned, for example, are mineral or organic acids, for instance hydrochloric acid, orthophosphoric acid, sulphuric acid, carboxylic acids, for instance acetic acid, tartaric acid, citric acid or lactic acid, and sulphonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of formula (II) below:

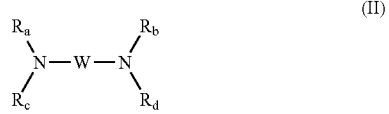

(II)

in which W is a propylene residue optionally substituted with a hydroxyl group or a $C_1$–$C_4$ alkyl radical; $R_a$, $R_b$, $R_c$, and $R_d$, which may be identical or different, represent a hydrogen atom or a $C_1$–$C_4$ alkyl or $C_1$–$C_4$ hydroxyalkyl radical.

The dye composition according to the invention may be in various forms, such as in the form of liquids, creams or gels, or in any other form that is suitable for dyeing keratin fibres, and especially human hair.

The process of the present invention is a process in which the composition according to the present invention as defined above is applied to the fibres, in the presence of an oxidizing agent, for a time that is sufficient to develop the desired coloration. The colour may revealed at acidic, neutral or alkaline pH and the oxidizing agent may be added to the composition of the invention just at the time of use, or it may be introduced using an oxidizing composition containing it, applied simultaneously with or sequentially to the composition of the invention.

According to one particular embodiment, the composition according to the present invention is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibres. After a leave-in time of 3 to 50 minutes approximately and preferably 5 to 30 minutes approximately, the keratin fibres are rinsed, washed with shampoo, rinsed again and then dried.

The oxidizing agents conventionally used for the oxidation dyeing of keratin fibres are, for example, hydrogen peroxide, urea peroxide, alkali metal bromates, persalts such as perborates and persulphates, peracids, and oxidase enzymes, among which mention may be made of peroxidases, 2-electron oxidoreductases such as uricases, and 4-electron oxygenases, for instance laccases. Hydrogen peroxide is particularly preferred.

The oxidizing composition may also contain various adjuvants conventionally used in hair dye compositions and as defined above.

The pH of the oxidizing composition containing the oxidizing agent is such that, after mixing with the dye composition, the pH of the resulting composition applied to the keratin fibres preferably ranges between 3 and 12 approximately and even more preferably between 5 and 11. It may be adjusted to the desired value by means of acidifying or basifying agents usually used in the dyeing of keratin fibres and as defined above.

The ready-to-use composition that is finally applied to the keratin fibres may be in various forms, such as in the form of liquids, creams or gels, or in any other form that is suitable for dyeing keratin fibres, and especially human hair.

The composition of the invention may be in the form of a kit. Such a kit comprises a composition as defined above on the one hand, and an oxidizing composition on the other hand.

A subject of the invention is also a multi-compartment device, in which a first compartment contains the dye composition of the present invention defined above and a second compartment contains an oxidizing agent. This device may be equipped with a means for applying the desired mixture to the hair, such as the devices described in patent FR 2 586 913 in the name of the Applicant.

Using this device, it is possible to dye keratin fibres using a process that involves mixing a dye composition of the invention with an oxidizing agent, and applying the mixture obtained to the keratin fibres for a time that is sufficient to develop the desired coloration.

Finally, a subject of the present invention is the 6-alkoxy-2,3-diaminopyridine compounds of formula (I), and the corresponding addition salts thereof as defined above.

These compounds may be synthesized according to the following synthetic scheme:

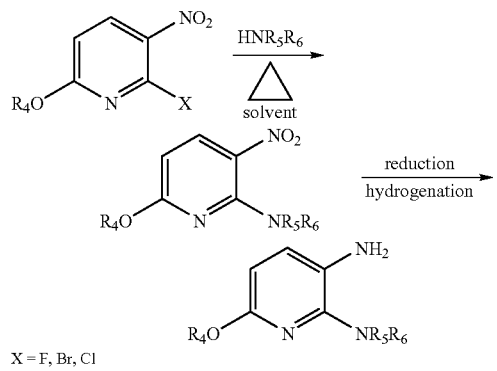

X = F, Br, Cl

The first step consists in reacting a 6-alkoxy-3-nitro-2-halopyridine derivative with an amine of the type $HNR_5R_6$ in which $R_5$ and $R_6$ have the same meanings given above, in a polar solvent with a boiling point of between 70° C. and 180° C. The reaction temperature varies, according to the pyridine derivatives and the nucleophilic amine, from 75° C. to 140° C. The solvent that will be chosen is preferably alcohols such as ethanol, isopropanol, butanol or pentanol, and also acetic acid, formic acid, dioxane or DMF.

The second step is a reduction reaction performed either by hydrogenation under heterogeneous catalysis, or by hydrogen transfer, or alternatively with metal hydrides or with a formic acid/acetic acid couple in the presence of palladium.

For example, the method, widely illustrated in the literature, of hydrogenation catalyzed with palladium(0), Pd (II) or Raney nickel or $PtO_2$, is used.

The hydrogen-transfer reduction by reacting cyclohexene in the presence of palladium is also found to be very effective.

The examples that follow serve to illustrate the invention without, however, being limiting in nature.

EXAMPLES OF SYNTHESIS

Example 1

2-(3-Amino-6-methoxy-2-pyridylamino)propane-1,3-diol

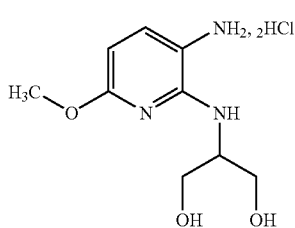

A) Synthesis of 2-(6-methoxy-3-nitro-2-pyridylamino)propane-1,3-diol 4 g (0.0212 mol) of the product 2-chloro-3-nitro-6-methoxypyridine, 40 ml of ethanol and 3.86 g (0.042 mol) of 2-aminopropane-1,3-diol are placed in a fully equipped round-bottomed flask. The mixture is refluxed for 2 hours with stirring and is then poured onto an ice/water mixture with stirring. The precipitate formed is filtered off by suction and dried under vacuum to constant weight. 4.54 g of yellow powder are obtained, ie a yield of 88.2%.

B) Synthesis of 2-(3-amino-6-methoxy-2-pyridylamino)propane-1,3-diol 4.48 g (0.0184 mol) of the product 2-(6-methoxy-3-nitro-2-pyridylamino)propane-1,3-diol synthesized according to procedure (A) above, 50 ml of ethanol, 10 ml of cyclohexene and 2 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 4.1 g of powder are obtained, ie a yield of 89%.

Analysis by mass spectrometry and magnetic resonance spectroscopy is in accordance with the expected structure.

Example 2

3-(3-Amino-6-methoxy-2-pyridylamino)propane-1,2-diol

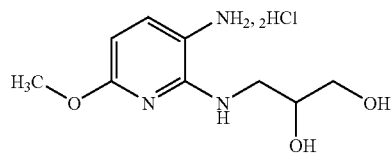

A) Synthesis of 3-(6-methoxy-3-nitro-2-pyridylamino)propane-1,2-diol 4 g (0.0212 mol) of the product 2-chloro-3-nitro-6-methoxypyridine, 50 ml of ethanol and 3.9 g (0.0424 mol) of racemic 3-aminopropane-1,2-diol are placed in a fully equipped round-bottomed flask. The mixture is refluxed for 2 hours with stirring and is then poured onto an ice/water mixture with stirring. The precipitate formed is filtered off by suction and dried under vacuum to constant weight. 2.19 g of yellow powder are obtained, ie a yield of 43%.

Analysis by mass spectrometry and magnetic resonance spectroscopy is in accordance with the expected structure.

B) Synthesis of 3-(3-amino-6-methoxy-2-pyridylamino)propane-1,2-diol 2 g (0.008 mol) of the product 3-(6-methoxy-3-nitro-2-pyridylamino)propane-1,2-diol synthesized according to procedure (A) above, 30 ml of ethanol, 10 ml of cyclohexene and 1.1 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 1.74 g of powder are obtained, ie a yield of 85%.

Analysis by mass spectrometry and magnetic resonance spectroscopy is in accordance with the expected structure.
Weight analysis:
Found: C, 38.5; H, 6.02; N, 14.91; O, 17.29; Cl, 23.87.
Calculated: C, 37.78; H, 5.99; N, 14.68; O, 16.77; Cl, 24.78.

Example 3

N-[2-(3-amino-6-methoxy-2-pyridylamino)ethyl] acetamide

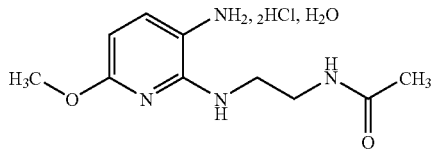

A) Synthesis of N-[2-(6-methoxy-3-nitro-2-pyridylamino) ethyl]acetamide 4 g (0.0212 mol) of the product 2-chloro-3-nitro-6-methoxypyridine, 50 ml of ethanol and 4.51 ml (0.0424 mol) of N-acetylethane-1,2-diamine are placed in a fully equipped round-bottomed flask. The mixture is refluxed for 2 hours with stirring and is then poured onto an ice/water mixture with stirring. The precipitate formed is filtered off by suction and dried under vacuum to constant weight. 3.9 g of yellow powder are obtained, ie a yield of 72.5%.

B) Synthesis of N-[2-(3-amino-6-methoxy-2-pyridylamino) ethyl]acetamide 3.87 g (0.0152 mol) of the product N-[2-(6-methoxy-3-nitro-2-pyridylamino)ethyl]acetamide synthesized according to procedure (A) above, 50 ml of ethanol, 10 ml of cyclohexene and 1.5 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 3.96 g of orange powder are obtained, ie a yield of 100%.

Analysis by mass spectrometry and magnetic resonance spectroscopy is in accordance with the expected structure.
Weight analysis:
Found: C, 37.52; H, 5.96; N, 18.29; O, 16.03; Cl, 23.89.
Calculated: C, 38.11; H, 6.40; N, 17.77; O, 15.23; Cl, 22.50.

Example 4

N2-(3-dimethylaminopropyl)-6-methoxypyridine-2,3-diamine

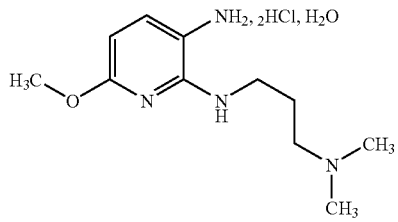

A) Synthesis of N-(6-methoxy-3-nitro-2-pyridyl)-N',N'-dimethylpropane-1,3-diamine 4 g (0.0212 mol) of the product 2-chloro-3-nitro-6-methoxypyridine, 40 ml of ethanol and 5.33 ml (0.0424 mol) of 3-dimethylaminopropylamine are placed in a fully equipped round-bottomed flask. The mixture is refluxed for 2 hours with stirring and is then poured onto an ice/water mixture with stirring. The precipitate formed is filtered off by suction and dried under vacuum to constant weight. 4.2 g of yellow powder are obtained, ie a yield of 78.1%.

B) Synthesis of N2-(3-dimethylaminopropyl)-6-methoxypyridine-2,3-diamine 4 g (0.0157 mol) of the product N-(6-methoxy-3-nitro-2-pyridyl)-N',N'-dimethylpropane-1,3-diamine synthesized according to procedure (A) above, 40 ml of ethanol, 10 ml of cyclohexene and 2 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 4.2 g of powder are obtained, ie a yield of 100%.

Analysis by mass spectrometry and magnetic resonance spectroscopy is in accordance with the expected structure.
Weight analysis:
Found: C, 41.54; H, 7.59; N, 17.33; O, 9.54; Cl, 24.41.
Calculated: C, 41.91; H, 7.67; N, 17.77; O, 10.15; Cl, 22.49.

Example 5

N2-(2-dimethylaminoethyl)-6-methoxypyridine-2,3-diamine

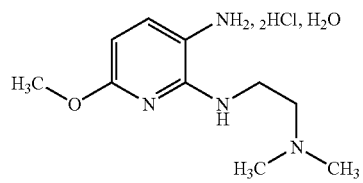

A) Synthesis of N-(6-methoxy-3-nitro-2-pyridyl)-N',N'-dimethylethane-1,2-diamine 4 g (0.0212 mol) of the product 2-chloro-3-nitro-6-methoxypyridine, 40 ml of ethanol and 3.85 ml (0.0424 mol) of N,N-dimethylethylenediamine are placed in a fully equipped round-bottomed flask. The mixture is refluxed for 2 hours with stirring and is then poured onto an ice/water mixture with stirring. The precipitate formed is filtered off by suction and dried under vacuum to constant weight. 54.027 g of yellow powder are obtained, ie a yield of 79.1%.

B) Synthesis of N2-(2-dimethylaminoethyl)-6-methoxypyridine-2,3-diamine 3.2 g (0.0133 mol) of the product N-(6-methoxy-3-nitro-2-pyridyl)-N',N'-dimethylethane-1,2-diamine synthesized according to procedure (A) above, 40 ml of ethanol, 10 ml of cyclohexene and 1.5 g of palladium-on-charcoal are placed in a fully equipped round-bottomed flask. The mixture is refluxed for 2 hours with stirring, the catalyst is then removed by filtration and the filtrate is then acidified with hydrochloric acid. After dilution with diisopropyl ether, the precipitate formed is filtered off by suction and dried under vacuum to constant weight. 1.204 g of powder are obtained, ie a yield of 37%.

Analysis by mass spectrometry and magnetic resonance spectroscopy is in accordance with the expected structure.

Weight analysis:

Found: C, 40.44; H, 7.2; N, 18.63; O, 9.97; Cl, 24.01.
Calculated: C, 39.88; H, 7.36; N, 18.60; O, 10.62; Cl, 23.54.

Examples 6 to 9

The following 6-alkoxy-2,3-diaminopyridine compounds were obtained according to the process described for Example 1B, starting with the nitro compounds indicated in the table below.

| | Nitro compounds | 6-Alkoxy-2,3-diaminopyridine compounds according to the invention | Found mass | Theoretical mass |
|---|---|---|---|---|
| Ex.6 | (structure) | (structure) | 213 | 213.24 |
| Ex.7 | (structure) | (structure) | 185 | 185.20 |
| Ex.8 | (structure) | (structure) | 252 | 252.32 |
| Ex.9 | (structure) | (structure) | 237 | 237.30 |

Starting from each of the 6-alkoxy-2,3-diaminopyridine compounds whose synthesis is presented above, the following dye compositions were prepared.

EXAMPLES OF DYEING

Example 1 of Dyeing in Acidic Medium

The dye composition below was prepared:

| | |
|---|---|
| N,N-Bis-(2-hydroxyethyl)para-phenylenediamine | $5 \times 10^{-3}$ mol |
| N-[2-(3-amino-6-methoxy-2-pyridylamino)-ethyl]acetamide | $5 \times 10^{-3}$ mol |
| Dye support | (1) |
| Demineralized water qs | 100 g |

(1) Dye support

| | |
|---|---|
| 96° ethanol | 20 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $Na_2HPO_4$ | 0.28 g |
| $KH_2PO_4$ | 0.46 g |

The composition is mixed at the time of use with an equal weight of 20-volumes aqueous hydrogen peroxide solution (6% by weight). A final pH of 7 is obtained.

The mixture obtained is applied to locks of grey hair containing 90% white hairs. After a leave-in time of 30 minutes, the locks are washed with a standard shampoo, rinsed and then dried.

Each lock is evaluated before and after dyeing in the L*a*b* system, using a Minolta® CM 2002 spectrophotometer (luminant D65).

In the L*a*b* space, the lightness is indicated by the value L* on a scale from 0 to 100, while the chromatic coordinates are expressed by a* and b*, which indicate two colour axes, a* the red-green axis, and b* the yellow-blue axis. According to this system, the higher the value of L*, the lighter and weaker the colour. Conversely, the lower the value of L*, the darker or stronger the colour.

The dyeing results below were obtained:

| Natural hair | | | Permanent-waved hair | | |
|---|---|---|---|---|---|
| L* | a* | b* | L* | a* | b* |
| 46.54 | 0.44 | 3.02 | 32.76 | 0.43 | −0.65 |

Examples 2 to 7 of Dyeing in Alkaline Medium

The dye compositions were prepared in the following proportions:

| | Example | | | | | |
|---|---|---|---|---|---|---|
| | 2 | 3 | 4 | 5 | 6 | 7 |
| 3-(3-amino-6-methoxy-2-pyridylamino)propane-1,2-diol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — |
| Benzene-1,4-diamine hydrochloride | — | $10^{-3}$ mol | — | — | — | — |
| 2-[(4-Aminophenyl)(2-hydroxyethyl)amino]ethanol sulphate | — | — | $10^{-3}$ mol | — | — | — |
| 2-Ethyl-5-methyl-2H-pyrazole-3,4-diamine hydrochloride | — | — | — | $10^{-3}$ mol | — | — |
| 5-Methylpyrazolo[1,5-a]pyrimidine-3,7-diamine hydrochloride | — | — | — | — | $10^{-3}$ mol | — |
| 2-(4,5-Diaminopyrazol-1-yl)ethanol hydrochloride | — | — | — | — | — | $10^{-3}$ mol |
| Dye support (2) | (*) | (*) | (*) | (*) | (*) | (*) |
| Demineralized water qs | 100 g | 100 g | 100 g | 100 g | 100 g | 100 g |

(*) Dye support (2) pH 9.5

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| | Example | | | | | |
|---|---|---|---|---|---|---|
| | 2 | 3 | 4 | 5 | 6 | 7 |
| Shade observed | red-brown | strong blue-violet grey | strong blue-green | green-grey | strong blue-violet | strong violet |

Examples 8 to 14 of Dyeing in Alkaline Medium

The dye compositions were prepared in the following proportions:

|  | Example | | | | | | |
| --- | --- | --- | --- | --- | --- | --- | --- |
|  | 8 | 9 | 10 | 11 | 12 | 13 | 14 |
| 2-(3-Amino-6-methoxy-pyrid-2-yl-amino)-cyclohexanol | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)-(2-hydroxyethyl)-amino]ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (2) | (*) | (*) | (*) | (*) | (*) | (*) | (*) |
| Demineralized water qs | 100 g | 100 g | 100 g | 100 g | 100 g | 100 g | 100 g |

(*) Dye support (2) pH 9.5

| | |
| --- | --- |
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

|  | Example | | | | | | |
| --- | --- | --- | --- | --- | --- | --- | --- |
|  | 8 | 9 | 10 | 11 | 12 | 13 | 14 |
| Shade observed | Intense grey | Intense blue-grey | Intense blue-green | Intense green | Green-yellowish grey | Blue-greenish grey | Intense violet | Intense violet |

Examples 15 to 19 of Dyeing in Alkaline Medium

The dye compositions were prepared in the following proportions:

|  | Example | | | | |
| --- | --- | --- | --- | --- | --- |
|  | 15 | 16 | 17 | 18 | 19 |
| 6-Methoxy-N2-(2-morpholin-4-ylethyl)pyridine-2,3-diamine | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — |
| Benzene-1,4-diamine hydrochloride | — | $10^{-3}$ mol | — | — | — |
| 2-[(4-Aminophenyl)-(2-hydroxyethyl)amino]ethanol sulphate | — | — | $10^{-3}$ mol | — | — |
| 5-Methylpyrazolo[1,5-a]-pyrimidine-3,7-diamine hydrochloride | — | — | — | $10^{-3}$ mol | — |
| 2-(4,5-Diaminopyrazol-1-yl)ethanol hydrochloride | — | — | — | — | $10^{-3}$ mol |
| Dye support (2) | (*) | (*) | (*) | (*) | (*) |
| Demineralized water qs | 100 g | 100 g | 100 g | 100 g | 100 g |

(*) Dye support (2) pH 9.5

| | |
| --- | --- |
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

|  | Example | | | | |
| --- | --- | --- | --- | --- | --- |
|  | 15 | 16 | 17 | 18 | 19 |
| Shade observed | Red-brown | Intense grey | Blue-green | Intense blue-violet | Violet |

Examples 20 to 23 of Dyeing in Alkaline Medium

The dye compositions were prepared in the following proportions:

|  | Example | | | |
|---|---|---|---|---|
|  | 20 | 21 | 22 | 23 |
| N2-(2-Fluoroethyl)-6-methoxypyridine-2,3-diamine | $10^{-3}$ mol | $10^{-3}$ mol | $10^{-3}$ mol | $10^{-3}$ mol |
| Benzene-1,4-diamine hydrochloride | $10^{-3}$ mol | — | — | — |
| 2-[(4-Aminophenyl)-(2-hydroxyethyl)amino]-ethanol sulphate | — | $10^{-3}$ mol | — | — |
| 5-Methylpyrazolo[1,5-a]-pyrimidine-3,7-diamine hydrochloride | — | — | $10^{-3}$ mol | — |
| 2-(4,5-Diaminopyrazol-1-yl)ethanol hydrochloride | — | — | — | $10^{-3}$ mol |
| Dye support (2) | (*) | (*) | (*) | (*) |
| Demineralized water qs | 100 g | 100 g | 100 g | 100 g |

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| $C_8$–$C_{10}$ alkyl polyglucoside as an aqueous 60% solution | 3.6 g AM |
| Benzyl alcohol | 2.0 g |
| Polyethylene glycol containing 8 ethylene oxide units | 3.0 g |
| $NH_4Cl$ | 4.32 g |
| Aqueous ammonia containing 20% $NH_3$ | 3.2 g |

(*) Dye support (2) pH 9.5

Each composition is mixed at the time of use with an equal weight of 20-volumes aqueous hydrogen peroxide solution (6% by weight). A final pH of 9.5 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

|  | Example | | | |
|---|---|---|---|---|
|  | 20 | 21 | 22 | 23 |
| Shade observed | Red-brown | Brown | Strong red | Red |

Examples 24 to 30 of Dyeing in Alkaline Medium

The dye compositions were prepared in the following proportions:

|  | Example | | | | | | |
|---|---|---|---|---|---|---|---|
|  | 24 | 25 | 26 | 27 | 28 | 29 | 30 |
| 3-(3-amino-6-methoxy-2-pyridylamino)propane-1,2-diol | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (3) | (*) | (*) | (*) | (*) | (*) | (*) | (*) |
| Demineralized water qs | 100 g | 100 g | 100 g | 100 g | 100 g | 100 g | 100 g |

(*) Dye support (3) pH 7

| | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

|  | Example | | | | | | |
|---|---|---|---|---|---|---|---|
|  | 24 | 25 | 26 | 27 | 28 | 29 | 30 |
| Shade observed | Strong orange-brown | Strong grey | Strong grey | Grey | Green-yellowish grey | Strong grey | Strong grey |

Examples 31 to 35 of Dyeing in Acidic Medium

The dye compositions were prepared in the following proportions:

|  | Example | | | | |
|---|---|---|---|---|---|
|  | 31 | 32 | 33 | 34 | 35 |
| N2-(2-Fluoroethyl)-6-methoxypyridine-2,3-diamine | $10^{-3}$ mol | $10^{-3}$ mol | $10^{-3}$ mol | $10^{-3}$ mol | $10^{-3}$ mol |
| Benzene-1,4-diamine hydrochloride | $10^{-3}$ mol | — | — | — | — |
| 2-[(4-Aminophenyl)-(2-hydroxyethyl)amino]ethanol sulphate | — | $10^{-3}$ mol | — | — | — |
| 2-Ethyl-5-methyl-2H-pyrazole-3,4-diamine hydrochloride | — | — | $10^{-3}$ mol | — | — |
| 5-Methylpyrazolo[1,5-a]pyrimidine-3,7-diamine hydrochloride | — | — | — | $10^{-3}$ mol | — |
| 2-(4,5-diaminopyrazol-1-yl)ethanol hydrochloride | — | — | — | — | $10^{-3}$ mol |
| Dye support (3) | (*) | (*) | (*) | (*) | (*) |
| Demineralized water qs | 100 g | 100 g | 100 g | 100 g | 100 g |

(*) Dye support (3) pH 7

| 96° ethanol | 20.8 g |
|---|---|
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

|  | Example | | | | |
|---|---|---|---|---|---|
|  | 31 | 32 | 33 | 34 | 35 |
| Shade observed | Strong brown-red | Brown | Orange-brown | Strong red-grey | Red |

Examples 36 to 42 of Dyeing in Acidic Medium

The dye compositions were prepared in the following proportions:

|  | Example | | | | | | |
|---|---|---|---|---|---|---|---|
|  | 36 | 37 | 38 | 39 | 40 | 41 | 42 |
| 6-Methoxy-N2-(2-morpholin-4-ylethyl)pyridine-2,3-diamine | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (3) | (*) | (*) | (*) | (*) | (*) | (*) | (*) |
| Demineralized water qs | 100 g | 100 g | 100 g | 100 g | 100 g | 100 g | 100 g |

(*) Dye support (3) pH 7

96° ethanol     20.8 g

-continued

| | |
|---|---|
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

The following dyeing results were obtained.

| | Example | | | | | | |
|---|---|---|---|---|---|---|---|
| | 36 | 37 | 38 | 39 | 40 | 41 | 42 |
| Shade observed | Strong orange-brown | Strong grey | Strong blue-grey | Green-yellowish grey | Green-grey | Strong grey | Strong grey |

Each composition is mixed at the time of use with an equal weight of 20-volumes aqueous hydrogen peroxide solution (6% by weight). A final pH of 7 is obtained.

Each mixture obtained is applied to grey hair containing 90% white hairs. After a leave-in time of 30 minutes, the hair is rinsed, washed with a standard shampoo, rinsed again and then dried.

Examples 43 to 49 of Dyeing in Acidic Medium

The dye compositions were prepared in the following proportions:

| | Example | | | | | | |
|---|---|---|---|---|---|---|---|
| | 43 | 44 | 45 | 46 | 47 | 48 | 49 |
| 2-(3-amino-6-methoxy-2-pyridylamino)-cyclohexanol | $10^{-3}$ mol | $10^{-3}$ mol | $10^{-3}$ mol | $10^{-3}$ mol | $10^{-3}$ mol | $10^{-3}$ mol | $10^{-3}$ mol |
| 4-Aminophenol | $10^{-3}$ mol | — | — | — | — | — | — |
| Benzene-1,4-diamine hydrochloride | — | $10^{-3}$ mol | — | — | — | — | — |
| 2-[(4-Aminophenyl)(2-hydroxyethyl)amino]-ethanol sulphate | — | — | $10^{-3}$ mol | — | — | — | — |
| Pyrimidine-2,4,5,6-tetraamine sulphate | — | — | — | $10^{-3}$ mol | — | — | — |
| 2-Ethyl-5-methyl-2H-pyrazole-3,4-diamine hydrochloride | — | — | — | — | $10^{-3}$ mol | — | — |
| 5-Methylpyrazolo[1,5-a]pyrimidine-3,7-diamine hydrochloride | — | — | — | — | — | $10^{-3}$ mol | — |
| 2-(4,5-Diaminopyrazol-1-yl)ethanol hydrochloride | — | — | — | — | — | — | $10^{-3}$ mol |
| Dye support (3) | (*) | (*) | (*) | (*) | (*) | (*) | (*) |
| Demineralized water qs | 100 g | 100 g | 100 g | 100 g | 100 g | 100 g | 100 g |

| (*) Dye support (3) pH 7 | |
|---|---|
| 96° ethanol | 20.8 g |
| Sodium metabisulphite as an aqueous 35% solution | 0.23 g AM |
| Pentasodium salt of diethylenetriaminepentaacetic acid as an aqueous 40% solution | 0.48 g AM |
| Sodium metabisulphite as an aqueous 35% solution | 3.6 g AM |
| Benzyl alcohol | 2.0 g |
| Polyethylene glycol containing 8 ethylene oxide units | 3.0 g |
| $KH_2PO_4$ | 0.28 g |
| $NaH_2PO_4$ | 0.47 g |

The following dyeing results were obtained.

| | Example | | | | | | |
|---|---|---|---|---|---|---|---|
| | 43 | 44 | 45 | 46 | 47 | 48 | 49 |
| Shade observed | strong brown | strong grey | strong blue-grey | grey | strong green-grey | strong brown | strong grey |

The invention claimed is:

1. A dye composition comprising, in a medium that is suitable for dyeing:
at least one oxidation base, and
at least one 6-alkoxy-2,3-diaminopyridine coupler of formula (I), and the addition salts thereof:

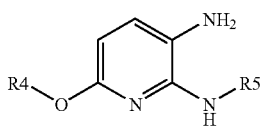

(I)

wherein:
R$_4$ is chosen from linear and branched C$_1$–C$_4$ alkyl radicals optionally substituted with at least one radical chosen from hydroxyl, C$_1$–C$_2$ alkoxy, and NR$_7$R$_8$ radicals wherein R$_7$ and R$_8$ are chosen from hydrogen, C$_1$–C$_4$ alkyl, C$_2$–C$_6$ (poly)hydroxyalkyl, C$_2$–C$_6$ (poly)aminoalkyl, and C$_2$–C$_6$ aminohydroxyalkyl radicals; and
R$_5$ is chosen from linear and branched C$_1$–C$_6$ alkyl radicals substituted with at least one radical chosen from C$_1$–C$_2$ alkoxy, hydroxyl, carboxyl, sulphonic (—SO$_3$H), NR$_9$R$_{10}$, hydroxyalkoxy, acylamino, and halogeno radicals; and 2-hydroxyethyloxyethyl radicals, wherein when R$_5$ is chosen from linear and branched C$_1$–C$_6$ alkyl radicals and is substituted with hydroxyl or with alkoxy, then R$_5$ carries a second radical,
wherein R$_9$ and R$_{10}$, which are identical or different, are chosen from hydrogen atoms; and from C$_1$–C$_4$ alkyl radicals optionally substituted with at least one radical chosen from hydroxyl, amino, C$_1$–C$_2$ monoalkylamino, C$_1$–C$_2$ dialkylamino, alkoxy and acylamino radicals, wherein in the acylamino radicals RCONH, R is chosen from C$_1$–C$_4$ alkyl radicals; alternatively, R$_9$ and R$_{10}$ may form, together with the nitrogen atom to which they are attached, a heterocycle comprising at least one atom chosen from nitrogen, oxygen, and sulphur.

2. The dye composition according to claim 1, wherein R$_5$ is chosen from C$_1$–C$_4$ alkyl radicals substituted with at least one radical chosen from hydroxyl, C$_1$–C$_2$ alkoxy, amino, C$_1$–C$_2$ monoalkylamino, C$_1$–C$_2$ dialkylamino, carboxyl, and sulphonic radicals.

3. The dye composition according to claim 1, wherein R$_5$ is an alkyl radical substituted with a radical chosen from amino, monoalkylamino, and dialkylamino radicals.

4. The dye composition according to claim 1, wherein R$_5$ is chosen from disubstituted alkyl radicals.

5. The dye composition according to claim 1, wherein R$_5$ is chosen from dihydroxyalkyl, acetamidoalkyl and dialkylaminoalkyl radicals, and from alkyl radicals substituted with a hydroxyl radical and an amino radical.

6. The dye composition according to claim 1, wherein R$_4$ is chosen from C$_1$–C$_4$ alkyl radicals optionally substituted with at least one radical chosen from hydroxyl and C$_1$–C$_2$ alkoxy radicals.

7. The dye composition according to claim 6, wherein R$_4$ is chosen from C$_1$–C$_4$ alkyl radicals.

8. The dye composition according to claim 1, wherein the compound of formula (I) is chosen from:
2-(3-amino-6-methoxypyrid-2-ylamino)propane-1,3-diol;
3-(3-amino-6-methoxypyrid-2-ylamino)propane-1,2-diol;
N-[2-(3-amino-6-methoxypyrid-2-ylamino)ethyl]acetamide;
N2-(3-dimethylaminopropyl)-6-methoxypyridine-2,3-diamine;
N2-(2-dimethylaminoethyl)-6-methoxypyridine-2,3-diamine;
N2-(2-fluoroethyl)-6-methoxypyridine-2,3-diamine;
6-methoxy-N2-(2-morpholin-4-ylethyl)pyridine-2,3-diamine;
2-(3-amino-6-methoxypyrid-2-ylamino)cyclohexanol;
and the addition salts thereof.

9. The dye composition according to claim 1, wherein the at least one oxidation base is chosen from para-phenylenediamines, bis(phenyl)alkylenediamines, para-aminophenols, bis-para-aminophenols, ortho-aminophenols, heterocyclic bases, and the addition salts thereof.

10. The dye composition according to claim 1, wherein the at least one oxidation base is present in an amount ranging from 0.001% to 10% by weight, relative to the total weight of the dye composition.

11. The dye composition according to claim 10, wherein the at least one oxidation base is present in an amount ranging from 0.005% to 6% by weight, relative to the total weight of the dye composition.

12. The dye composition according to claim 1, further comprising at least one additional coupler chosen from meta-phenylenediamines, meta-aminophenols, meta-diphenols, naphthalene-based couplers, and heterocyclic couplers other than the couplers of formula (I).

13. The dye composition according to claim 12, wherein for the at least one coupler of formula (I) and for the at least one additional coupler, if present, each coupler is present in an amount ranging from 0.001% to 10% by weight, relative to the total weight of the dye composition.

14. The dye composition according to claim 13, wherein for the at least one coupler of formula (I) and for the at least one additional coupler, if present, each coupler is present in an amount ranging from 0.005% to 6% by weight, relative to the total weight of the dye composition.

15. The dye composition according to claim 1, wherein the medium suitable for dyeing is a cosmetic medium that is suitable for dyeing keratin fibers.

16. The dye composition according to claim 1, further comprising at least one oxidizing agent.

17. A process for the oxidation dyeing of keratin fibers comprising applying to the fibers, in the presence of at least one oxidizing agent, for a time that is sufficient to allow a desired color to be obtained, a dye composition comprising, in a medium that is suitable for dyeing:
at least one oxidation base, and
at least one 6-alkoxy-2,3-diaminopyridine coupler of formula (I), and the addition salts thereof:

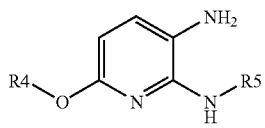

wherein:
- $R_4$ is chosen from linear and branched $C_1$–$C_4$ alkyl radicals optionally substituted with at least one radical chosen from hydroxyl, $C_1$–$C_2$ alkoxy, and $NR_7R_8$ radicals wherein $R_7$ and $R_8$ are chosen from hydrogen, $C_1$–$C_4$ alkyl, $C_2$–$C_6$ (poly)hydroxyalkyl, $C_2$–$C_6$ (poly)aminoalkyl, and $C_2$–$C_6$ aminohydroxyalkyl radicals; and
- $R_5$ is chosen from linear and branched $C_1$–$C_6$ alkyl radicals substituted with at least one radical chosen from $C_1$–$C_2$ alkoxy, hydroxyl, carboxyl, sulphonic (—$SO_3H$), $NR_9R_{10}$, hydroxyalkoxy, acylamino, and halogeno radicals; and 2-hydroxyethyloxyethyl radicals; wherein when $R_5$ is chosen from linear and branched $C_1$–$C_6$ alkyl radicals and is substituted with hydroxyl or with alkoxy, then $R_5$ carries a second radical,
- wherein $R_9$ and $R_{10}$, which are identical or different, are chosen from hydrogen atoms; and from $C_1$–$C_4$ alkyl radicals optionally substituted with at least one radical chosen from hydroxyl, amino, $C_1$–$C_2$ mono- or dialkylamino, alkoxy and acylamino radicals, wherein in the acylamino radicals RCONH, R is chosen from $C_1$–$C_4$ alkyl radicals; alternatively, $R_9$ and $R_{10}$ may form, together with the nitrogen atom to which they are attached, a heterocycle comprising at least one atom chosen from nitrogen, oxygen, and sulphur.

18. The process according to claim 17, wherein the at least one oxidizing agent is chosen from hydrogen peroxide, urea peroxide, alkali metal bromates, persalts, peracids, and oxidase enzymes.

19. The process according to claim 17, wherein the at least one oxidizing agent is mixed with the dye composition at the time of application.

20. The process according to claim 17, wherein the at least one oxidizing agent is applied to the fibers simultaneously with or sequentially to the dye composition, in the form of an oxidizing composition.

21. A multi-compartment kit comprising a first dye compartment comprising a dye composition comprising, in a medium that is suitable for dyeing:
- at least one oxidation base, and
- at least one 6-alkoxy-2,3-diaminopyridine coupler of formula (I), and the addition salts thereof:

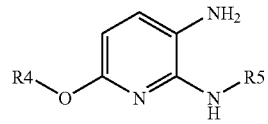

wherein:
- $R_4$ is chosen from linear and branched $C_1$–$C_4$ alkyl radicals optionally substituted with at least one radical chosen from hydroxyl, $C_1$–$C_2$ alkoxy, and $NR_7R_8$ radicals wherein $R_7$ and $R_8$ are chosen from hydrogen, $C_1$–$C_4$ alkyl, $C_2$–$C_6$ (poly)hydroxyalkyl, $C_2$–$C_6$ (poly)aminoalkyl, and $C_2$–$C_6$ aminohydroxyalkyl radicals; and
- $R_5$ is chosen from linear and branched $C_1$–$C_6$ alkyl radicals substituted with at least one radical chosen from $C_1$–$C_2$ alkoxy, hydroxyl, carboxyl, sulphonic (—$SO_3H$), $NR_9R_{10}$, hydroxyalkoxy, acylamino, and halogeno radicals; and 2-hydroxyethyloxyethyl radicals; wherein when $R_5$ is chosen from linear and branched $C_1$–$C_6$ alkyl radicals and is substituted with hydroxyl or with alkoxy, then $R_5$ carries a second radical,
- wherein $R_9$ and $R_{10}$, which are identical or different, are chosen from hydrogen atoms; and from $C_1$–$C_4$ alkyl radicals optionally substituted with at least one radical chosen from hydroxyl, amino, $C_1$–$C_2$ mono- or dialkylamino, alkoxy and acylamino radicals, wherein in the acylamino radicals RCONH, R is chosen from $C_1$–$C_4$ alkyl radicals; alternatively, $R_9$ and $R_{10}$ may form, together with the nitrogen atom to which they are attached, a heterocycle comprising at least one atom chosen from nitrogen, oxygen, and sulphur; and
- a second compartment comprising an oxidizing composition.

* * * * *